US007347199B1

(12) United States Patent
Lewis et al.

(10) Patent No.: US 7,347,199 B1
(45) Date of Patent: *Mar. 25, 2008

(54) PRESSURISED METERED DOSE INHALERS (MDI)

(75) Inventors: David Lewis, Parma (IT); David Ganderton, Parma (IT); Brian Meakin, Bath (GB); Paolo Ventura, Parma (IT); Gaetano Brambilla, Parma (IT); Raffaella Garzia, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/831,888

(22) PCT Filed: Nov. 23, 1999

(86) PCT No.: PCT/EP99/09002

§ 371 (c)(1),
(2), (4) Date: Jul. 19, 2001

(87) PCT Pub. No.: WO00/30608

PCT Pub. Date: Jun. 2, 2000

(30) Foreign Application Priority Data

Nov. 25, 1998 (IT) .............................. MI98A2559
Jul. 30, 1999 (IT) .............................. MI99A1712

(51) Int. Cl.
*A61M 16/00* (2006.01)
(52) U.S. Cl. .............................. 128/200.23; 128/203.15
(58) Field of Classification Search ........... 128/200.11, 128/200.12, 200.14, 200.23, 203.12, 203.15, 128/200.24; 420/49, 52, 582; 239/338; 424/45, 46
See application file for complete search history.

(56) References Cited

U.S. PATENT DOCUMENTS

| 3,361,306 A | * | 1/1968 | Grim ..................... 222/402.13 |
| 3,622,053 A | * | 11/1971 | Ryden ..................... 222/402.1 |
| 4,185,100 A | | 1/1980 | Rovee et al. |
| 4,499,108 A | | 2/1985 | Sequeira et al. |
| 4,579,854 A | * | 4/1986 | Iwakuma et al. ........... 514/312 |
| 4,835,145 A | | 5/1989 | MacDonald |
| 5,192,528 A | | 3/1993 | Radhakrishnan et al. |
| 5,415,853 A | | 5/1995 | Hettche et al. |
| 5,435,297 A | * | 7/1995 | Klein ..................... 128/200.23 |
| 5,605,674 A | | 2/1997 | Purewal et al. |
| 5,642,728 A | | 7/1997 | Andersson et al. |
| 5,653,961 A | | 8/1997 | McNally et al. |
| 5,676,930 A | * | 10/1997 | Jager et al. ..................... 424/45 |
| 5,683,677 A | * | 11/1997 | Purewal et al. ............... 424/45 |
| 5,695,743 A | * | 12/1997 | Purewal et al. ............... 424/45 |
| 5,891,419 A | | 4/1999 | Cutie |
| 5,954,047 A | * | 9/1999 | Armer et al. .......... 128/200.23 |
| 5,955,058 A | | 9/1999 | Jager et al. |
| 6,004,537 A | | 12/1999 | Blondino et al. |
| 6,006,745 A | * | 12/1999 | Marecki ................. 128/200.23 |
| 6,026,808 A | * | 2/2000 | Armer et al. .......... 128/200.23 |
| 6,045,778 A | | 4/2000 | Jager et al. |
| 6,131,566 A | * | 10/2000 | Ashurst et al. ......... 128/200.14 |
| 6,143,277 A | * | 11/2000 | Ashurst et al. ............... 424/45 |
| 6,149,892 A | * | 11/2000 | Britto ......................... 424/45 |
| 6,150,418 A | | 11/2000 | Hochrainer et al. |
| 6,241,969 B1 | | 6/2001 | Saidi et al. |
| 6,253,762 B1 | * | 7/2001 | Britto ..................... 128/200.14 |
| 6,290,930 B1 | | 9/2001 | Blondino et al. |
| 6,315,985 B1 | | 11/2001 | Wu et al. |
| 6,413,496 B1 | | 7/2002 | Goodman et al. |
| 6,451,285 B2 | | 9/2002 | Blondino et al. |
| 6,645,466 B1 | | 11/2003 | Keller et al. |
| 7,018,618 B2 | * | 3/2006 | Lewis et al. ................... 424/45 |
| 2003/0077230 A1 | | 4/2003 | Blondino et al. |
| 2003/0157028 A1 | | 8/2003 | Lewis et al. |
| 2003/0190267 A1 | | 10/2003 | Lewis et al. |
| 2003/0190287 A1 | | 10/2003 | Lewis et al. |
| 2003/0190289 A1 | | 10/2003 | Lewis et al. |
| 2003/0206870 A1 | | 11/2003 | Lewis et al. |
| 2005/0129621 A1 | | 6/2005 | Davies et al. |
| 2005/0142071 A1 | | 6/2005 | Lewis et al. |
| 2005/0152846 A1 | | 7/2005 | Davies et al. |
| 2005/0154013 A1 | | 7/2005 | Davies et al. |
| 2005/0220718 A1 | | 10/2005 | Lewis et al. |

FOREIGN PATENT DOCUMENTS

| EP | 0 372 777 | 6/1990 |
| EP | 0 504 112 A2 | 9/1992 |
| EP | 0 642 992 | 3/1995 |

(Continued)

OTHER PUBLICATIONS

R.O. Williams, III, et al., *European Journal of Pharmaceutics and Biopharmaceutics*, vol. 44, pp. 195-203 (1997).

(Continued)

*Primary Examiner*—Teena Mitchell
(74) *Attorney, Agent, or Firm*—Oblon, Spivak, McClelland, Maier & Neustadt, P.C.

(57) ABSTRACT

The invention relates to the use of pressurized metered dose inhalers (MDIs) having part or all of their internal surfaces consisting of stainless steel, anodised aluminum or lined with an inert organic coating; and to compositions to be delivered with said MDIs.

32 Claims, No Drawings

FOREIGN PATENT DOCUMENTS

| EP | 0 653 204 | 5/1995 |
|---|---|---|
| EP | 0 911 048 | 4/1999 |
| GB | 1 525 181 | 9/1978 |
| GB | 2 326 334 | 12/1998 |
| WO | WO 91/11173 | 8/1991 |
| WO | WO 92/11236 | 7/1992 |
| WO | WO 92/20391 | 11/1992 |
| WO | WO 93/05765 | 4/1993 |
| WO | WO 93/11747 | 6/1993 |
| WO | WO 93/18746 | 9/1993 |
| WO | WO 94/13262 | 6/1994 |
| WO | WO 94/14490 | 7/1994 |
| WO | WO 94/21228 | 9/1994 |
| WO | WO 94/21229 | 9/1994 |
| WO | WO 95/17195 | 6/1995 |
| WO | WO 96/18384 | 6/1996 |
| WO | WO 96/19198 | 6/1996 |
| WO | WO 96/19968 | 7/1996 |
| WO | WO 96/19969 | 7/1996 |
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 97/47286 | 12/1997 |
| WO | WO 98/01147 | 1/1998 |
| WO | WO 98/03533 | 1/1998 |
| WO | WO 98/05302 | 2/1998 |
| WO | WO 98/13031 | 4/1998 |
| WO | WO 98/24420 | 6/1998 |
| WO | WO 98/34595 | 8/1998 |
| WO | WO 98/34596 | 8/1998 |
| WO | WO 98/56349 | 12/1998 |
| WO | WO 91/12596 | 3/1999 |
| WO | WO 99/64014 | 12/1999 |
| WO | WO 99/65460 | 12/1999 |
| WO | WO 99/65464 | 12/1999 |
| WO | WO 00/06121 | 2/2000 |
| WO | WO 00/07567 | 2/2000 |
| WO | WO 00/23065 | 4/2000 |
| WO | WO 00/30608 | 6/2000 |
| WO | WO 00/35458 | 6/2000 |
| WO | WO 00/53157 | 9/2000 |
| WO | WO 00/78286 | 12/2000 |
| WO | WO 01/47493 | 7/2001 |
| WO | WO 93/11743 | 6/2003 |

OTHER PUBLICATIONS

U.S. Appl. No. 10/766,857, filed Jan. 30, 2004, Lewis et al.

B. Meakin, "Fine Particle Dose Control of Solution Based pMDIs", *Drug Delivery to the Lungs IX*, The Aerosol Society, pp. 1-20, (Dec. 14 & 15, 1998).

*ABPI Compendium of Data Sheets and Summaries of Product Characteristics*, Datapharm Publications Limited, London, pp. 81-82, (1996-1997).

Paul A. Sanders, Ph.D., "Homogeneous Systems and Their Properties", *Handbook of Aerosol Technology*, Second Edition, Van Nostrand Reinhold Company, NY, p. 30, 1979.

G. Brambilla et al, "Modulation of Aerosol Clouds Produced by HFA Solution Inhalers", *Portable Inhalers*, pp. 1559-159, (Nov. 26 & 27, 1998).

U.S. Appl. No. 09/831,888, filed Jul. 19, 2001, Lewis et al.

S.S. Davis, "Physico-Chemical Studies on Aerosol Solutions For Drug Delievery I. Water-Propylene glycol Systems", *International Journal of Pharmaceutics*, 1, 1978, pp. 71-83.

L. Harrison et al, "Twenty-eight-day Double-blind Safety Study of an HFA-134a Inhalation Aerosol System in Healthy Subjects", *J. Pharm. Pharmacol.*, 1996, vol. 48, pp. 596-600.

P. Hoet et al, "Epidemic of liver disease caused by hydrochlorofluorocarbons used as ozone-sparing substitutes of chlorofluorocarbons", *The Lancet*, 1997, vol. 350, pp. 555-559.

J. Daly, Jr., "Properties and toxicology of CFC alternatives", *Aerosol Age*, Feb. 1990, pp. 26-27, 40, 56 and 57.

D. Strobach, "Alternatives to CFCs" Part II, *Aerosol Age*, Jul. 1988, pp. 32-33, 42 and 43.

Tsi-Zong Tzou et al, "Drug Form Selection in Albuterol-Containing Metered-Dose Inhaler Formulations and Its Impact on Chemical and Physical Stability", *Journal of Pharmaceutical Sciences*, 1997, vol. 86, No. 12, pp. 1352-1357.

M.J. Kontny et al, "Issues Surrounding MDI Formulation Development with Non-CFC Propellants", *Journal of Aerosol Medicine*, 1991, vol. 4, No. 3, pp. 181-187.

I. P. Tansey, "Changing to CFC-Free Inhalers: The Technical and Clinical Challenges", *The Pharmaceutical Journal*, 1997, vol. 259, pp. 896-898.

D. Tiwari et al, Compatibility Evaluation of Metered-Dose Inhaler Valve Elastomers with Tetrafluoroethane (P134a), a Non-CFC Propellant, *Drug Development and Industrial Pharmacy*, 1998, vol. 24, No. 4, pp. 345-352.

*Handbook of Pharmaceutical Excipients*, 3rd Ed., Kibbe Editor, pp. 7-9, 220-222, 234-235 and 560-561.

L. I. Harrison et al, "Pharmacokinetics and Dose Proportionality of Beclomethasone From Three Strengths of A CFC-Free Beclomethasone Dipropionate Metered-Dose Inhaler", *Biopharmaceutics & Drug Disposition*, 1997, vol. 18, No. 7, pp. 635-643.

Chet Leach, "Enhanced Drug Delivery Through Reformulating MDIs with HFA Propellants-Drug Deposition and Its Effect on Preclinical and Clinical Programs", *Respiratory Drug Delivery V*, 1996, pp. 133-144.

U.S. Appl. No. 11/289,479, filed Nov. 30, 2005, Lewis et al.

U.S. Appl. No. 10/531,867, filed Sep. 16, 2005, Church et al.

U.S. Appl. No. 09/147,669, filed Feb. 24, 1999, Lewis et al.

U.S. Appl. No. 10/546,619, filed Aug. 23, 2005, Razzetti et al.

* cited by examiner

PRESSURISED METERED DOSE INHALERS (MDI)

The invention relates to the use of pressurised metered dose inhalers (MDIs) having part or all of their internal surfaces consisting of stainless steel, anodised aluminium or lined with an inert organic coating. The invention also relates to compositions to be delivered with said MDIs.

Pressurised metered dose inhalers are well known devices for administering pharmaceutical products to the respiratory tract by inhalation.

Active materials commonly delivered by inhalation include bronchodilators such as β2 agonists and anticholinergics, corticosteroids, anti-leukotrienes, anti-allergics and other materials that may be efficiently administered by inhalation, thus increasing the therapeutic index and reducing side effects of the active material.

MDI uses a propellant to expel droplets containing the pharmaceutical product to the respiratory tract as an aerosol.

For many years the preferred propellants used in aerosols for pharmaceutical use have been a group of chlorofluorocarbons which are commonly called Freons or CFCs, such as $CCl_3F$ (Freon 11 or CFC-11), $CCl_2F_2$ (Freon 12 or CFC-12), and $CClF_2$—$CClF_2$ (Freon 114 or CFC-114).

Recently, the chlorofluorocarbon (CFC) propellants such as Freon 11 and Freon 12 have been implicated in the destruction of the ozone layer and their production is being phased out.

Hydrofluoroalkanes [(HFAs) known also as hydro-fluorocarbons (HFCs)] contain no chlorine and are considered less destructive to ozone and these are proposed as substitutes for CFCs.

HFAs and in particular 1,1,1,2-tetrafluoroethane (HFA 134a) and 1,1,1,2,3,3,3-heptafluoropropane (HFA 227) have been acknowledged to be the best candidates for non-CFC propellants and a number of medicinal aerosol formulations using such HFA propellant systems have been disclosed.

Many of these applications, in which HFAs are used as propellant, propose the addition of one or more of adjuvants including compounds acting as co-solvents, surface active agents including fluorinated and non-fluorinated surfactants, dispersing agents including alkylpolyethoxylates and stabilizers.

In the international application no PCT/EP98/03533 filed on Oct. 6, 1998 the applicant described solution compositions for use in an aerosol inhaler, comprising an active material, a propellant containing a hydrofluoroalkane (HFA), a cosolvent and further comprising a low volatility component to increase the mass median aerodynamic diameter (MMAD) of the aerosol particles on actuation of the inhaler.

Compositions for aerosol administration via MDIs can be solutions or suspensions. Solution compositions offer several advantages: they are convenient to manufacture being completely dissolved in the propellant vehicle and obviate physical stability problems associated with suspension compositions.

The widespread use of these formulations is limited by their chemical instability, causing the formation of degradation products.

WO94/13262 proposes the use of acids as stabilisers preventing the chemical degradation of the active ingredient in aerosol solution formulations comprising HFAs. Among the selected medicaments ipratropium bromide is comprised, for which many composition examples are supplied, in which the active ingredient is in combination with an organic or inorganic acid.

WO96/32099, WO96/32150, WO96/32151 and WO96/32345 disclose metered dose inhalers for the administration of different active ingredients in suspension in the propellant, wherein the internal surfaces of the inhaler are partially or completely coated with one or more fluorocarbon polymers optionally in combination with one or more non-fluorocarbon polymers.

Said applications do not however address the technical problem of the chemical stability of the active ingredient but they rather concern a different problem, namely that of the adhesion of micronized particles of the suspended active ingredient to the internal surfaces of the inhaler, such as the can walls, valves and sealings. It is also known from Eur. J. Pharm. Biopharm. 1997, 44, 195 that suspensions of drugs in HFA propellant are frequently subjected to absorption of the drug particles on the valves and on the internal walls of the inhaler. The properties of an epoxy phenol resin coating of the aerosol cans have been studied to circumvent this problem.

WO 95/17195 describes aerosol compositions comprising flunisolide, ethanol and HFA propellants. It is stated in the document that conventional aerosol canisters can be used to contain the composition and that certain containers enhance its chemical and physical stability. It is suggested that the composition can be preferably contained in vials coated with resins such as epoxy resins (e.g. epoxy-phenolic resins and epoxy-urea-formaldehyde resins).

Actually the results reported in Tables 5, 6 and 8 respectively on pages 16 and 19 of the cited application demonstrate that flunisolide decomposes only in plastic cans (Table 8), and that the percent drug recovery in compositions stored in aluminium, glass or epoxy-phenol formaldehyde resin coated vials is practically the same (Table 8). In other words there is no difference between aluminium, glass type III or epoxy/phenol-formaldehyde resin coated aluminium vials coated by Cebal. No data are reported for other types of epoxy resins.

It has now been found that the chemical stability problems of active ingredients in solution in HFA propellants can be eliminated by storing and delivering said composition employing metered-dose inhalers having part or all of their internal metallic surfaces consisting of stainless steel, anodised aluminium or lined with an inert organic coating.

The preferred material for the aerosol cans is anodised aluminium.

In the case of epoxy-phenol resin coating the choice of the suitable coating will be opportunely made on the basis of the characteristics of the active ingredient.

The most widely used epoxy resins in can coatings are produced by the reaction of epichlorohydrin and bisphenol A (DGEBPA). Variations in the molecular weight and in the polymerisation degree result in resins of different properties.

Phenoxy resins are other commercially important thermoplastic polymers derived from bisphenols and epichlorohydrin, characterized in that their molecular weights (MWs) are higher, ie, ca 45000, than those of conventional epoxy resins, ie, 8000 and lack terminal epoxide functionality.

Other multifunctional resins are epoxy-phenol-novolac and epoxy-cresol-novolac resins obtained by glycidylation of the phenol-formaldehyde (novolac) or of the o-cresol-formaldehyde (o-cresol novolac) condensates respectively.

The inhalers according to the invention effectively prevent the chemical degradation of the active ingredient.

Surprisingly and contrary to what reported in the prior art with regard to flunisolide, we found a considerable degradation of the tested active ingredients when their formulations were stored in glass containers type III.

SUMMARY OF THE INVENTION

Pressurised metered dose inhalers for dispensing solution of an active ingredient in a hydrofluorocarbon propellant, a co-solvent and optionally a low-volatility component characterized in that part or all of the internal surfaces of said inhalers consist of stainless steel, anodised aluminium or are lined with an inert organic coating.

DETAILED DESCRIPTION OF THE INVENTION

Pressurised metered dose inhalers are known devices, usually consisting of a main body or can, acting as a reservoir for the aerosol formulation, a cap sealing the main body and a metering valve fitted in the cap.

MDIs are usually made of a conventional material such as aluminium, tin plate, glass, plastic and the like.

According to the invention, part or all of the internal surfaces of the inhalers consists of stainless steel, anodised aluminium or is lined with an inert organic coating. One of the preferred coating consists of epoxy-phenol resin. Any kind of stainless steel may be used. Suitable epoxy-phenol resins are commercially available.

Active ingredients which may be used in the aerosol compositions to be dispensed with the inhalers of the invention are any ingredient which can be administered by inhalation and which meets problems of chemical stability in solution in HFA propellants giving rise to a decomposition when stored in conventional materials cans and in particular in aluminium cans.

In the compositions to be delivered with the MDIs of the invention the hydrofluorocarbon propellant is preferably selected from the group of HFA 134a, HFA 227 and mixtures thereof.

The co-solvent is usually an alcohol, preferably ethanol. The low volatility component, when present, is selected from the group of glycols, particularly propylene glycol, polyethylene glycol and glycerol, alkanols such as decanol (decyl alcohol), sugar alcohols including sorbitol, mannitol, lactitol and maltitol, glycofural (tetrahydro-furfurylalcohol) and dipropylene glycol, vegetable oils, organic acids for example saturated carboxylic acids including lauric acid, myristic acid and stearic acid; unsaturated carboxylic acids including sorbic acid, and especially oleic acid; saccharine, ascorbic acid, cyclamic acid, amino acids, or aspartame, esters for example ascorbyl palmitate, isopropyl myristate and tocopherol esters; alkanes for example dodecane and octadecane; terpenes for example menthol, eucalyptol, limonene; sugars for example lactose, glucose, sucrose; polysaccharides for example ethyl cellulose, dextran; antioxidants for example butylated hydroxytoluene, butylated hydroxyanisole; polymeric materials for example polyvinyl alcohol, polyvinyl acetate, polyvinyl pyrrolidone; amines for example ethanolamine, diethanolamine, triethanolamine; steroids for example cholesterol, cholesterol esters. The low-volatility component has a vapour pressure at 25° C. lower than 0.1 kPa, preferably lower than 0.05 kPa.

The aerosols compositions to be delivered with the pressurised MDIs of the invention may contain from 0.2 to 2% by weight of said low volatility component.

Propylene glycol, polyethylene glycol, isopropyl myristate and glycerol are particularly preferred low-volatility components.

The function of the low volatility component is to modulate the MMAD of the aerosol particles. Being used at very low concentrations, it does not substantially affect the chemical stability of the compositions.

Examples of active ingredients include: anticholinergics such as ipratropium bromide, oxitropium bromide, tiotropium bromide; acetal corticosteroids such as budesonide, ciclesonide, rofleponide; chetal corticosteroids such as flunisolide, triamcinolone acetonide; other corticosteroids such as fluticasone propionate, mometasone furoate; short or long acting beta-adrenergic agonists such as salbutamol, formoterol, salmeterol, TA 2005 and their combinations. The active ingredients when possible may be present in racemic mixtures or in form of a single enantiomer or epimer.

As said before, WO 94/13262 teaches that problems of chemical stability of medicaments and in particular of ipratropium bromide in aerosol solution compositions can be solved adding an acid, either an inorganic acid or an organic acid, to the HFA propellant/cosolvent system.

Examples of compositions containing ipratropium bromide in HFA 134a/ethanol systems further containing an inorganic acid such as hydrochloric, nitric, phosphoric or sulfuric acid or an organic acid such as ascorbic or citric acid are provided.

We found that in solution compositions comprising ipratropium bromide, a propellant containing a hydrofluoroalkane, a cosolvent and further comprising a low volatility component:

a) different decomposition rates occur with different acids: for example we found that ipratropium bromide (20 µg/dose) in a composition of 13% (w/w) ethanol, 1.0% (w/w) glycerol, 20 µl/can of 1N hydrochloric acid and HFA 134a to 12 ml/can rapidly decomposes and after 3 months storage at 40° C. gives 85.0% average of drug remaining;

b) ipratropium bromide with or without acids is stable in stainless steel, anodised aluminium or in some types of epoxy phenol resin lined cans;

c) surprisingly certain kinds of materials, such as glass, coatings proposed in the prior-art to overcome the physical absorption phenomenon of the active ingredient, such as perfluoroalkoxyalkanes and fluorinated-ethylene-propylene polyether sulfone resins, or certain kinds of epoxy phenol coatings turned out to be completely unsatisfactory and ineffective in preventing its chemical degradation.

Another preferred active ingredient for the preparation of solution compositions in a HFA/cosolvent system to be dispensed by MDIs according to the present invention is budesonide.

Previously HFA/budesonide compositions have been described, in which budesonide is present in suspension in the propellant system and the composition further comprises additional ingredients such as particular kinds of surfactants (EP 504112, WO 93/05765, WO 93/18746, WO 94/21229).

In WO 98/13031 it is reported that suspension formulations of budesonide have a propensity to rapidly form coarse flocs upon dispersion and redispersion which may deleteriously affect dosage reproducibility. There is also a tendency for budesonide to deposit from suspension onto the walls of the container.

To achieve stable suspensions of particulate budesonide it is employed in the prior art a composition containing a mixture of HFA propellants to match the density of the propellant mixture to be substantially identical to the density of budesonide, up to 3% of an adjuvant such as ethanol and small amounts of surfactant.

It is stated in the document that the levels of the adjuvants are low to avoid significant solubilization of drug, leading to a problem of chemical degradation and particle size increase on storage.

In the solution compositions of the present invention budesonide is chemically and physically stable.

The aerosol compositions of the invention distributed in inhalers having the internal surfaces consisting of stainless steel, anodised aluminium or coated with an inert material and preferably with epoxy-phenol resin are stable for long periods and do not undergo chemical degradation.

Also in this case a considerable degradation of the active ingredient was noticed when glass containers were used.

Analogously flunisolide and dexbudesonide (the 22R-epimer of budesonide) solutions in HFA propellant containing ethanol and a low-volatility component are stable when stored in inhalers having the internal surfaces consisting of anodised aluminium or coated with epoxy-phenol resin. Evident degradation of flunisolide was noticed when glass containers were used.

It has been also found that the low volatility component may also act as a co-solvent, thus increasing the solubility of the drug in the formulation and increasing the physical stability and/or allowing the possibility to decrease the quantity of co-solvent required.

The following examples further illustrate the invention. In the examples and tables the different types of epoxy phenol resins are indicated with numbers in brackets corresponding to:

(1) Epoxy-phenol lacquered aluminium vials coated by Cebal (2) Epoxy-phenol lacquered aluminium vials coated by Presspart (3) Epoxy-phenol lacquered aluminium vials coated by Nussbaum & Guhl (4) Epoxy-phenol lacquered aluminium vials coated by Presspart, other than (2)

EXAMPLE 1

A composition containing 4.8 mg of ipratropium bromide (20 μg/dose), 13% (w/w) ethanol, 1.0% (w/w) glycerol and HFA 134a to 12 ml/can was distributed in stainless steel, anodised aluminium, standard aluminium cans or in cans having different internal coatings and were stored at various conditions.

The results are reported in Table 1 and Table 2.

The percent drug remaining in the composition, measured by HPLC, shows that stainless steel and anodised aluminium cans as well as epoxy-phenol resins (1), (2) and (4) coated cans are effective in preventing the chemical degradation of ipratropium bromide, differently from glass cans or other tested coatings.

EXAMPLE 2

The effect of different acids on the chemical stability of the composition of Example 1 was studied.

Citric, ascorbic and hydrochloric acids were added to the formulations in the amounts reported in Table 3.

The stability of the compositions was tested after 1, 2 and 5 months storage at 40° C. in epoxy-phenol resin (4) coated cans.

EXAMPLE 3

Compositions containing 12 mg of budesonide (50 μg/dose), 13% or 15% (w/w) ethanol, 1.3% (w/w) glycerol in HFA 134a to 12 ml/can were distributed in stainless steel, anodised aluminium, standard aluminium, glass cans or in cans having different internal coatings and were stored at various conditions.

The results are reported in Table 4 and 5.

The percent drug remaining in the compositions, measured by HPLC, shows the favourable effect of stainless steel, anodised aluminium and inert coating on the chemical stability of the active ingredient in respect to standard aluminium or glass cans. The best results have been obtained with stainless steel, anodised aluminium cans and with epoxy-phenol or perfluoroalkoxyalkane coatings.

EXAMPLE 4

A composition containing 48 mg of dexbudesonide (200 μg/dose), 15% (w/w) ethanol, 1.3% (w/w) glycerol in HFA 134a to 12 ml can was distributed in epoxy-phenol lacquered aluminium cans and was stored at 40° C.

The percent drug remaining in the composition after 8 months, measured by HPLC, was 95.4% (average value referred to two tests).

The control of the epimeric distribution showed that there is no transfer from the 22R to the 22S epimer.

EXAMPLE 5

Compositions containing 7.2, 12, 16.8 mg of dexbudesonide (corresponding to 30, 50 and 70 μg/dose respectively), ethanol, 0.9 (w/w) PEG 400 or isopropyl myristate (IPM) in HFA 227 to 12 ml can was distributed in aluminium anodised cans and was stored 70 days at 50° C. The results are reported in Table 6.

The percent drug remaining in the composition measured by HPLC shows the favourable effect of anodised aluminium cans on the chemical stability of the active ingredient. The control of the epimeric distribution showed that there is no transfer from the 22R to the 22S epimer.

EXAMPLE 6

The fine particle dose (FPD: weight of particles having an aerodynamic diameter lower than 4.7 μm) of dexbudesonide solution compositions in HFA 134a or HFA 227, prepared following the examples 4 and 5, was determined.

The experiments were performed using the Andersen Cascade Impactor and the data obtained are average values from 10 shots.

The results, reported in Table 7 and 8 show that dexbudesonide formulations of the invention are characterized by a very low dose and a very high fine particle dose.

The FPD gives a direct measure of the mass of particles within the specified size range and is closely related to the efficacy of the product.

EXAMPLE 7

A composition containing 60 mg of flunisolide (250 μg/dose), 15% (w/w) ethanol, 1% (w/w) glycerol in HFA 134a to 12 ml/can was distributed in anodised aluminium, glass cans or in cans having different internal coatings and were stored for 41 days at 50° C.

The results are reported in Table 9.

The percent drug remaining in the composition, measured by HPLC, shows the favourable effect of anodised aluminium and inert coating with epoxy-phenol resins on the chemical stability of the active ingredient in respect to glass cans.

EXAMPLE 8

The solubility of ipratropium bromide and micronized budesonide in ethanol, glycerol and their mixtures has been investigated.

The tests were carried out at room temperature.

a) Solubility in Ethanol.

About 8.5 g of absolute ethanol were weighed into a flask. The active ingredient (Ipratropium Bromide or Budesonide) was added in small amounts, under magnetic stirrer, until no further dissolution occurred (i.e.: a saturated solution was obtained). The flask was stirred for about 40 minutes, and left to settle overnight prior to analysis, to let the system equilibrate. The flask was kept sealed, to avoid evaporation.

The solution obtained was then filtered and tested for the amount of active ingredient, according to the conventional analytical procedure.

B) Solubility in Ethanol/Glycerol Mixtures.

The required amounts of ethanol and glycerol were weighted into a flask, and mixed by a magnetic stirrer until a homogeneous phase was obtained.

The solubility of ipratropium bromide in ethanol is 42.48 mg/g.

The solubility data of ipratropium bromide in ethanol/glycerol mixtures are listed in Table 10.

The solubility of micronized budesonide in ethanol is 31.756 mg/g.

Solubility data of micronized budesonide in ethanol/glycerol mixtures are listed in Table 11.

The data show that both the tested active ingredients are rather soluble in ethanol, and that their solubility increases even when small percentages of glycerol are added.

The increase in solubility is maintained also in presence of HFA propellants.

TABLE 1

Percent ipratropium bromide (IPBr) recovered after storing the composition of Example 1 for 8 months at 40° C. in cans of different types

| CAN TYPE | % RESIDUAL IPBr |
|---|---|
| Epoxy-phenol resin (4) | 96 |
| Perfluoroalkoxyalkane | 57 |
| Fluorinated-ethylene-propylene/polyether sulphone (Xylan 8840[(R)]) | 78 |
| Stainless steel | 96 |
| Standard aluminium | 46 |

TABLE 2

Percent ipratropium bromide (IPBr) recovered after storing the composition of Example 1 for 30 and 60 days at 50° C., or for 96 days at 40° C. in cans of different types (average values referred to two tests).

| | | % RESIDUAL IPBr (% RESIDUAL IPBr RELATIVE TO t = 0) | | |
|---|---|---|---|---|
| CAN TYPE | t = 0 | t = 30 days at 50° C. | t = 60 days at 50° C. | t = 96 days at 40° C. |
| Epoxy phenol resin (1) | 99 | 89 (90) | 88.5 (89.5) | 93.5 (94.5) |
| Epoxy phenol resin (2) | 97.5 | 90 (92) | 88.5 (90.5) | 89 (91) |
| Epoxy phenol resin (3) | 98.5 | 56.5 (57.5) | 46 (47) | 52.5 (53.5) |
| Anodised aluminum | 94 | 89 (95) | 87 (92.5) | 90.5 (96.5) |
| Glass type III * | — | 48.5 (—) | 41.5 (—) | 47 (—) |

* according to Eur Pharmacopoeia 3rd Ed Suppl 1999

TABLE 3

Percent ipratropium bromide (IPBr) recovered after storing the compositions of Example 1, with different acids added, in epoxy-phenol (4) coated cans (average values referred to two tests)

| | | % RESIDUAL IPBr (% RESIDUAL IPBr RELATIVE TO t = 0) | | |
|---|---|---|---|---|
| Acid | t = 0 | t = 1 month at 40° C. | t = 2 months at 40° C. | t = 5 months at 40° C. |
| Citric | | | | |
| (0.6% w/w) | 98 | 98 (100) | 99 (101) | 94 (96) |
| (0.3% w/w) | 99 | 99 (100) | 100 (101) | 97 (98) |
| (0.07% w/w) | 99 | 98 (99) | 99 (100) | 96 (97) |
| Ascorbic | 119 | 113 (95) | 112 (94) | 110 (92) |
| Hydrochloric | | | | |
| (4 μl-1N) | 101 | 100 (99) | 104 (102) | 96 (95) |
| (10 μl-1N) | 101 | 98 (97) | 98 (97) | 97 (96) |
| (20 μl-1N) | 100 | 95 (95) | 98 (98) | 97 (97) |
| None | 97 | 97 (100) | 98 (101) | 95 (98) |

TABLE 4

Percent budesonide recovered after storing the composition of Example 3 (13% ethanol) for 7 months at 40° C. in cans of different types

| CAN TYPE | % RESIDUAL BUDESONIDE |
|---|---|
| Epoxy-phenol resin (4) | 100 |
| Fluorinated-ethylene-propylene/polyether sulphone (Xylan 8840[(R)]) | 93.5 |
| Stainless steel | 97 |
| Aluminium | 68 |
| Perfluoroalkoxyalkane | 100 |

TABLE 5

Percent budesonide recovered after storing the composition of Example 3 (15% ethanol) for 33 and 73 days at 50° C. in cans of different types (average values referred to two tests).

| CAN TYPE | % RESIDUAL BUDESONIDE (% RESIDUAL BUDESONIDE RELATIVE TO t = 0) | | |
|---|---|---|---|
| | t = 0 | T = 33 days | t = 73 days |
| Epoxy phenol resin (1) | 99.3 | 97.0 (97.7) | 95.4 (96.1) |
| Epoxy phenol resin (2) | 99.5 | 96.6 (97.0) | 95.6 (96.1) |
| Epoxy phenol resin (3) | 99.3 | 96.6 (97.2) | 95.9 (96.5) |
| Anodised aluminium | 99.9 | 99.2 (99.3) | 97.7 (97.8) |
| Glass type III * | — | 86.15 (—) | 80.4 (—) |

* according to Eur Pharmacopoeia 3$^{rd}$ Ed Suppl 1999

These results have been confirmed storing the same formulation up to 7 months at 30° C., 40° C., 45° C. and 50° C.

TABLE 6

Percent dexbudesonide recovered after storing the compositions of Example 5 for 70 days at 50° C. in anodised aluminium cans (average values referred to two tests).

| Metered dose (μg) | Ethanol % (w/w) | Low vol. comp. 0.9% (w/w) | % Residual dexbudesonide (% residual dexbudesonide relative to t = 0) | |
|---|---|---|---|---|
| | | | t = 0 days | t = 70 days |
| 30 | 5 | PEG 400 | 95.8 | 95.8 (100) |
| | | IPM | 98.1 | 96.8 (98.7) |
| 50 | 8 | PEG 400 | 99.0 | 98.0 (98.9) |
| | | IPM | 98.0 | 99.4 (101) |
| 70 | 7 | PEG 400 | 95.7 | 93.75 (98.0) |
| | | IPM | 100.4 | 96.3 (96.0) |

IPM = Isopropyl myristate

TABLE 7

Fine particle dose (FPD) values of dexbudesonide solution formulation in HFA 134a containing:
dexbudesonide 14.4 mg/can (60 μg/shot)
ethanol 8% (w/w)
low volatility compound 0.9% (w/w)
HFA 134a to 12 ml can (valve chamber volume = 63 μl)
MMAD = 2.0 μm

| Low volatility Compound | FPD (μg) | FPF (%) | Metered dose (μg) | Delivered dose (μg) |
|---|---|---|---|---|
| IPM | 39.9 | 73.6 | 57.9 | 54.2 |
| IPM | 39.4 | 77.4 | 53.2 | 50.9 |

IPM = isopropyl myristate
FPF = fine particle fraction (Fine particle dose/Delivered dose × 100)
FPD = weight of particles having an aerodynamic diameter lower than 4.7 μm
Metered dose is given by the sum of delivered dose and actuator residue.
Delivered dose is the dose delivered ex actuator.

TABLE 8

Fine particle dose (FPD) values of dexbudesonide solution formulation in HFA 227 containing:
dexbudesonide 15.12 mg/can (63 μg/shot)
ethanol 7% (w/w)
low volatility compound 0.9% (w/w)
HFA 227 to 12 ml can (valve chamber volume = 63 μl)
MMAD = 2.0 μm

| Low volatility Compound | FPD (μg) | FPF (%) | Metered dose (μg) | Delivered dose (μg) |
|---|---|---|---|---|
| IPM | 45.0 | 75.5 | 63.9 | 59.7 |
| PEG 400 | 48.5 | 78.9 | 65.5 | 61.5 |

IPM = isopropyl myristate
FPF = fine particle fraction (Fine particle dose/Delivered dose × 100)
FPD = weight of particles having an aerodynamic diameter lower than 4.7 μm
Metered dose is given by the sum of delivered dose and actuator residue
Delivered dose is the dose delivered ex actuator

TABLE 9

Percent flunisolide recovered after storing the composition of Example 7 for 41 days at 50° C. in cans of different types (average values referred to two tests).

| CAN TYPE | % RESIDUAL FLUNISOLIDE (% RESIDUAL FLUNISOLIDE RELATIVE TO t = 0)) | | |
|---|---|---|---|
| | t = 0 | t = 41 days | t = 93 days |
| Epoxy phenol resin (1) | 98.4 | 99.2 (101) | 101.4 (103) |
| Epoxy phenol resin (2) | 101.9 | 99.7 (97.8) | 101.9 (100) |
| Epoxy phenol resin (3) | 101.7 | 99.2 (97.5) | 101.2 (99.6) |
| Anodised aluminum | 101.6 | 100.4 (98.8) | 100.7 (99.1) |
| Glass type III * | — | — | 97.5 (—) |

* according to Eur Pharmacopoeia 3$^{rd}$ Ed Suppl 1999

TABLE 10

Solubility of Ipratropium Bromide in ethanol/glycerol mixtures

| Ethanol (%) | Glycerol (%) | Ipratropium Bromide solubility (mg/g) |
|---|---|---|
| 100 | 0 | 42.8 |
| 92.6 | 7.4 | 74.0 |
| 91.9 | 8.1 | 74.7 |
| 91.3 | 8.7 | 90.5 |
| 88.4 | 11.6 | 98.0 |
| 82.6 | 17.4 | 115.6 |
| 71.4 | 28.6 | 196.7 |
| 60 | 40 | 271.6 |
| 40 | 60 | 307.2 |
| 21.1 | 78.9 | 265.7 |
| 0 | 100 | 73.4 |

TABLE 11

Solubility of micronized Budesonide in ethanol/glycerol mixtures

| Ethanol (%) | Glycerol (%) | Budesonide solubility (mg/g) |
|---|---|---|
| 100 | 0 | 31.756 |
| 92.5 | 7.5 | 36.264 |
| 91.9 | 8.1 | 36.277 |
| 91.3 | 8.7 | 37.328 |
| 87.7 | 12.3 | 38.364 |
| 83.3 | 16.7 | 37.209 |
| 71.4 | 28.6 | 35.768 |
| 60 | 40 | 28.962 |
| 39.9 | 60.1 | 14.840 |
| 21.1 | 78.9 | 3.990 |
| 0 | 100 | 0.214 |

The invention claimed is:

1. A pressurized metered dose inhaler, said inhaler containing a solution comprising an active ingredient, a hydrofluorocarbon propellant, and a cosolvent, wherein said inhaler has an internal surface and all or part of said internal surface is anodized aluminum.

2. The pressurized metered dose inhaler of claim 1, wherein said solution further comprises a low-volatility component.

3. The pressurized metered dose inhaler of claim 2, wherein said low-volatility component is selected from the group consisting of propylene glycol, glycerol, polyethylene glycol, and isopropyl myristate.

4. The pressurized metered dose inhaler of claim 1, wherein said active ingredient is selected from the group consisting of β2 agonists, steroids, anticholinergic agents, and mixtures thereof.

5. The pressurized metered dose inhaler of claim 1, wherein said active ingredient is selected from the group consisting of a β-adrenergic agonist, ipratropium bromide, oxitropium bromide, tiotropium bromide, flunisolide, triamcinolone acetonide, fluticasone propionate, mometasone furoate, budesonide, ciclesonide, rofleponide, and epimers thereof.

6. The pressurized metered dose inhaler of claim 5, wherein said β-adrenergic agonist is selected from the group consisting of salbutamol, formoterol, salmeterol, and TA 2005.

7. The pressurized metered dose inhaler of claim 1, wherein said co-solvent is ethanol.

8. The pressurized metered dose inhaler of claim 1, wherein said propellant is selected from the group consisting of HFA 227, HFA 134a, and mixtures thereof.

9. The pressurized metered dose inhaler of claim 1, wherein said solution further comprises a low-volatility component; said low-volatility component is selected from the group consisting of propylene glycol, glycerol, polyethylene glycol, and isopropyl myristate; said active ingredient is selected from the group consisting of a β-adrenergic agonist, ipratropium bromide, oxitropium bromide, tiotropium bromide, flunisolide, triamcinolone acetonide, fluticasone propionate, mometasone furoate, budesonide, ciclesonide, rofleponide, and epimers thereof; said co-solvent is ethanol; and said propellant is selected from the group consisting of HFA 227, HFA 134a, and mixtures thereof.

10. The pressurized metered dose inhaler of claim 9, wherein said β-adrenergic agonist is selected from the group consisting of salbutamol, formoterol, salmeterol, and TA 2005.

11. The pressurized metered dose inhaler of claim 9, wherein said active ingredient is ipratropium bromide.

12. The pressurized metered dose inhaler of claim 9, wherein said active ingredient is oxitropium bromide.

13. The pressurized metered dose inhaler of claim 9, wherein said active ingredient is tiotropium bromide.

14. The pressurized metered dose inhaler of claim 9, wherein said active ingredient is flunisolide.

15. The pressurized metered dose inhaler of claim 9, wherein said active ingredient is triamcinolone acetonide.

16. The pressurized metered dose inhaler of claim 9, wherein said active ingredient is fluticasone propionate.

17. The pressurized metered dose inhaler of claim 9, wherein said active ingredient is mometasone furoate.

18. The pressurized metered dose inhaler of claim 9, wherein said active ingredient is budesonide.

19. The pressurized metered dose inhaler of claim 9, wherein said active ingredient is ciclesonide.

20. The pressurized metered dose inhaler of claim 9, wherein said active ingredient is rofleponide.

21. The pressurized metered dose inhaler of claim 1, wherein said solution further comprises a low-volatility component; said low-volatility component is selected from the group consisting of propylene glycol, glycerol, polyethylene glycol, and isopropyl myristate; said active ingredient is selected from the group consisting of a β-adrenergic agonists agonist, ipratropium bromide, oxitropium bromide, tiotropium bromide, flunisolide, triamcinolone acetonide, fluticasone propionate, mometasone furoate, budesonide, ciclesonide, rofleponide, and epimers thereof; and said co-solvent is ethanol.

22. The pressurized metered dose inhaler of claim 21, wherein said active ingredient is ipratropium bromide.

23. The pressurized metered dose inhaler of claim 21, wherein said active ingredient is oxitropium bromide.

24. The pressurized metered dose inhaler of claim 21, wherein said active ingredient is tiotropium bromide.

25. The pressurized metered dose inhaler of claim 21, wherein said active ingredient is flunisolide.

26. The pressurized metered dose inhaler of claim 21, wherein said active ingredient is triamcinolone acetonide.

27. The pressurized metered dose inhaler of claim 21, wherein said active ingredient is fluticasone propionate.

28. The pressurized metered dose inhaler of claim 21, wherein said active ingredient is mometasone furoate.

29. The pressurized metered dose inhaler of claim 21, wherein said active ingredient is budesonide.

30. The pressurized metered dose inhaler of claim 21, wherein said active ingredient is ciclesonide.

31. The pressurized metered dose inhaler of claim 21, wherein said active ingredient is rofleponide.

32. The pressurized metered dose inhaler of claim 21, wherein said β-adrenergic agonist is selected from the group consisting of salbutamol, formoterol, salmeterol, and TA 2005.

* * * * *